United States Patent
Fujii

(10) Patent No.: US 7,303,542 B2
(45) Date of Patent: *Dec. 4, 2007

(54) MIXING/CHARGING PORT FOR MEDICAL TREATMENT

(75) Inventor: Ryoji Fujii, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 834 days.

This patent is subject to a terminal disclaimer.

(21) Appl. No.: 10/751,134

(22) Filed: Dec. 30, 2003

(65) Prior Publication Data

US 2004/0158201 A1    Aug. 12, 2004

Related U.S. Application Data

(63) Continuation of application No. 09/964,026, filed on Sep. 25, 2001, now Pat. No. 6,699,215.

(30) Foreign Application Priority Data

Sep. 26, 2000   (JP)   ............... 2000-292023

(51) Int. Cl.
*A61M 37/00*   (2006.01)
(52) U.S. Cl. ..................................... 604/82
(58) Field of Classification Search ........... 604/82, 604/83, 86–88, 167.01–167.06, 200–206, 604/236–237, 244, 246, 247, 905
See application file for complete search history.

(56) References Cited

U.S. PATENT DOCUMENTS

| 4,981,140 A | 1/1991 | Wyatt |
| 5,135,489 A | 8/1992 | Jepson et al. |
| 5,178,607 A | 1/1993 | Lynn et al. |
| 5,199,948 A | 4/1993 | McPhee |

(Continued)

FOREIGN PATENT DOCUMENTS

EP   0 499 401 A   8/1992

(Continued)

*Primary Examiner*—Manuel Mendez
(74) *Attorney, Agent, or Firm*—Hamre, Schumann, Mueller & Larson, P.C.

(57) ABSTRACT

A mixing/charging port for medical treatment capable of reliably absorbing air bubbles. The mixing/charging port for medical treatment includes a disc-like valve having an insertion hole at the center, a seating for supporting the lower part of the periphery of the valve with the center of the rear surface side of the valve not supported, and a cover for restraining the valve by covering at least the upper part of the periphery of the valve with the center on the front side surface of the valve left uncovered, wherein a fitting hole defined by an inner periphery of the cover works as an anchor for anchoring an insertion body to the mixing/charging port by fitting the insertion body to the fitting hole when the insertion body is inserted into the insertion hole; and the tip of the depressed part of the valve is brought into contact against the inner bottom surface of the seating when the valve is depressed by the insertion member.

6 Claims, 4 Drawing Sheets

U.S. PATENT DOCUMENTS

| | | | |
|---|---|---|---|
| 5,203,775 A | 4/1993 | Frank et al. |
| 5,279,571 A | 1/1994 | Larkin |
| 5,306,265 A | 4/1994 | Ragazzi |
| 5,324,256 A | 6/1994 | Lynn et al. |
| 5,417,673 A | 5/1995 | Gordon |
| 5,531,672 A | 7/1996 | Lynn |
| 5,603,706 A | 2/1997 | Wyatt et al. |
| 5,989,216 A | 11/1999 | Johnson et al. |
| 6,213,973 B1 | 4/2001 | Eliasen et al. |
| 6,468,251 B1 | 10/2002 | Yamanaka et al. |
| 6,699,215 B2 * | 3/2004 | Fujii | 604/82 |

FOREIGN PATENT DOCUMENTS

| | | |
|---|---|---|
| EP | 0 783 899 A2 | 7/1997 |
| EP | 1 040 845 A | 10/2000 |
| JP | 3-62113 | 9/1991 |
| JP | 4-200566 | 7/1992 |
| JP | 3066107 | 11/1999 |
| WO | 95/03841 A | 2/1995 |
| WO | 99/24108 A | 5/1999 |

* cited by examiner

MIXING/CHARGING PORT FOR MEDICAL TREATMENT

This application is a continuation of application Ser. No. 09/964,026, filed Sep. 25, 2001 now U.S. Pat. No. 6,699,215, which application(s) are incorporated herein by reference.

BACKGROUND OF THE INVENTION

1. Field of the Invention

The present invention relates to a mixing/charging port for medical treatment, which is placed on a medical instrument to make it easy and reliable to mix/charge solutions from the outside of a feeding passage or, on the other hand, to collect solutions from the inside of the feeding passage.

2. Description of the Prior Art

In infusing a drug solution or transfusing blood into a patient, it is often necessary to provide a main feeding passage with a side-infusing line in order to mix/charge different kinds of drug solutions or to collect the liquid flowing in the feeding passage as a sample. Conventionally, in this case, a feeding passage of an infusion set provided with a rubber mixing/charging port (cock) for piercing by needles is used and solutions are mixed/charged by piercing the mixing/charging port with an injection needle, etc.

However, in such a method, when piercing the site other than the predetermined piercing site of the mixing/charging port with the needle, the liquid may leak from the site. Another problem is that the injection needle may be contaminated due to a working error, etc. In order to fix and hold a luer, etc. to be inserted ("an insertion member" will be referred to hereinafter), recently, the mixing/charging port capable of holding an insertion member has been considered. An example includes a mixing/charging port equipped with a valve that opens when a male luer located at the tip of a syringe is inserted into the mixing/charging port to push the valve and which closes by itself when the luer is pulled out from the mixing/charging port.

However, in such a mixing/charging port, it is necessary to hold a luer at the mixing/charging port regardless of the state in which the valve is inserted (i.e., valve opens) or the state in which the valve is pulled out (i.e., valve closes). Therefore, there are the following various problems. More specifically, first, it is necessary to deepen a luer receiving part of the mixing/charging port. With such a shape, it is difficult to remove the liquid leaking from the valve, which easily may become unsanitary. Furthermore, in the mixing/charging port having such a deep luer receiving part, the liquid may begin to be mixed/charged in a state in which the luer is not sufficiently inserted into the valve. In this case, if the amount of drug solution to be mixed/charged is small, the administration of an effective amount of drug solution may not be carried out. Secondly, the structure of the valve becomes complicated, which may lead to increasing cost. Furthermore, as the structure of the valve is more complicated, failures are more likely to occur, and the valve is more likely to be broken.

On the other hand, in the conventional simple-structured mixing/charging port (for example, a mixing/charging port merely equipped with a disk-like valve made of an elastic member having a slit), it was difficult to insert a luer of a syringe into the mixing/charging port. If possible, it was difficult to hold the syringe reliably at the mixing/charging port. This is because the conventional disk-like valve is formed of a material having a large elasticity and has a simple structure in which the thick main body is merely provided with a slit, so that the valve exhibits a large resistance when the luer is inserted into the valve, and the valve is deformed largely when the valve holds the luer. However, if the thickness of the elastic member is reduced or a material having a small elasticity is used in order to reduce the resistance when the luer is inserted, the backflow prevention effect of the valve is lowered, which may cause liquid leaking.

In order to solve the above-mentioned problems, there has been a proposal of a mixing/charging port for medical treatment having a simple structure and capable of reliably holding an insertion member, which includes a disk-like valve having an insertion hole at the center, a seating for supporting the lower part of the periphery of the valve with the center of the rear surface side of the valve left unsupported, a cover for restraining the valve by covering at least the upper part of the periphery of the valve with the center on the front surface side of the valve left uncovered, and an anchor means for anchoring the insertion member to the mixing/charging port by inserting the insertion member into the insertion hole and by using the edge portion of the cover provided with a fitting hole.

FIGS. 1A, 1B and 1C are projection drawings from three directions of an example of a conventional mixing/charging port for medical treatment. That is, FIG. 1A is a longitudinal sectional view of a mixing/charging port; FIG. 1B is a cross sectional view of the mixing/charging port along line I-I in FIG. 1A; and FIG. 1C is a plan view of the mixing/charging port, respectively.

In FIG. 1, reference numeral 1 denotes a disk-like valve, 2 denotes a cover, and 3 denotes an insertion hole. Furthermore, reference numeral 4 denotes an insertion member, 5 denotes an annular rib, 6 denotes a fitting hole, 7 denotes a seating, 8 denotes a passage, and 9 denotes a hook. In this structure, the valve 1 is sandwiched between the hook 9 of the cover 2 and the annular rib 5.

However, in the above-mentioned mixing/charging port for medical treatment, there has been a problem in that when absorbing air bubbles generated inside the mixing/charging port from the insertion hole 3, air bubbles that enter between the depressed part of the valve 1 and the inner part of the mixing/charging port cannot be absorbed efficiently. Consequently, because of the presence of air bubbles that have not been able to be absorbed, there remains a possibility that an air bubble may be a contaminant when transfusing blood or infusing a liquid medicine into a patient, which may lead to a problem in that medical treatment cannot be carried out safely.

For example, when an insertion member 4 is inserted into a conventional mixing/charging port for medical treatment, the valve 1 is depressed and the insertion member 4 is held by the elastic force of the depressed part of the valve 1 and the fitting hole 6 as shown in the sectional view of FIG. 2. However, between the tip portion of the depressed part of the valve 1 and the seating 7, a certain region A is created. If air bubbles enter this region A, the air bubbles cannot be absorbed from an absorption port of the insertion member 4.

SUMMARY OF THE INVENTION

With the foregoing in mind, it is an object of the present invention to provide a mixing/charging port for medical treatment capable of reliably absorbing air bubbles that have been generated in or contaminate mixing/charging port.

In order to achieve the above-mentioned object, a mixing/charging port for medical treatment of the present invention includes a disk-like valve having an insertion hole at the center, a seating for supporting the lower part of the periphery of the valve with the center of the rear surface side of the valve left unsupported, and a cover for restraining the valve by covering at least the upper part of the periphery of the valve with the center of the front surface side of the valve left uncovered, wherein a fitting hole defined by an inner edge portion of the cover works as an anchor for anchoring an insertion member to the mixing/charging port in a way in which the insertion member is fitted to the fitting hole when the insertion member is inserted into the insertion hole; and the tip of the depressed part of the valve is brought into contact against the inner bottom surface of the seating when the valve is depressed with the insertion member.

According to such a configuration, air bubbles generated inside the mixing/charging port can be absorbed to the outside reliably by inserting the insertion member. Consequently, it is possible to reduce the risk of air bubbles being infused into the patient when transfusing blood or infusing a drug solution is carried out. Therefore, a medical treatment can be carried out safely.

DESCRIPTION OF THE PREFERRED EMBODIMENTS

Figure 3:
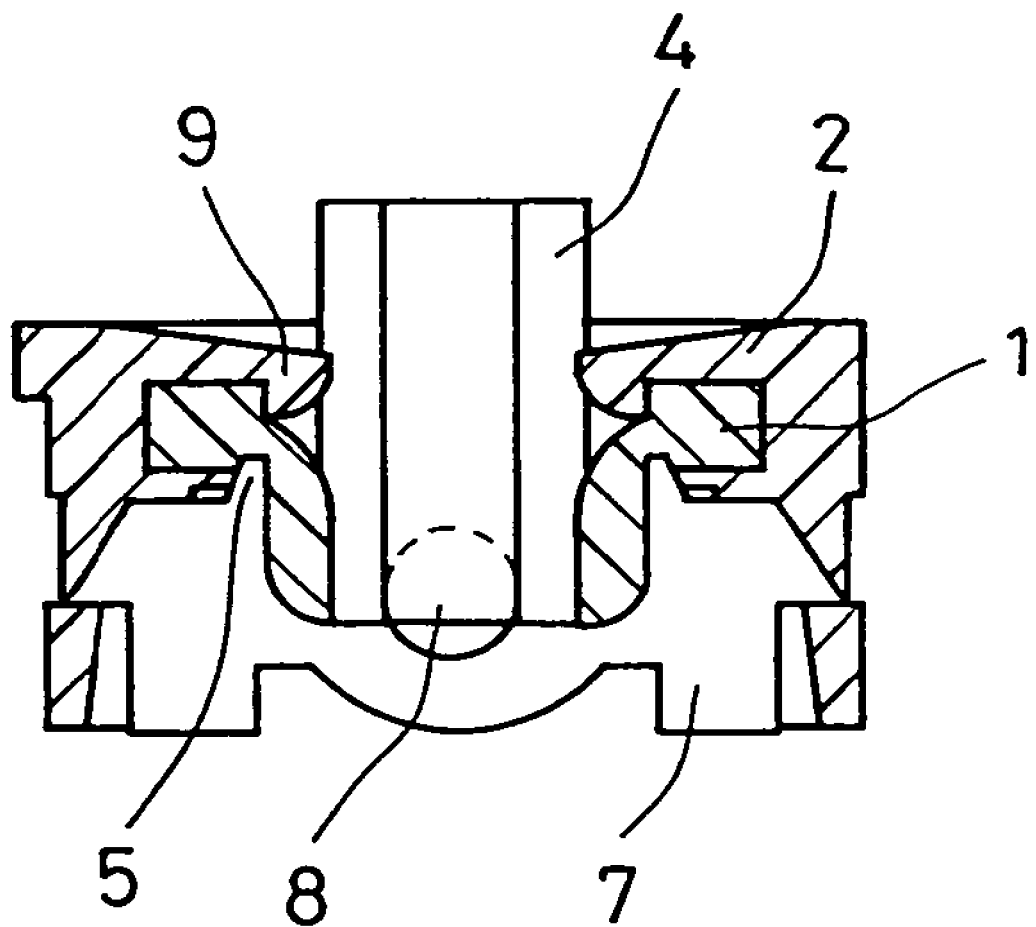
FIG. 3 is a cross-sectional view showing a mixing/charging port for medical treatment of an embodiment according to the present invention.

Hereinafter, the mixing/charging port for medical treatment of the present invention will be described by way of embodiments with reference to the accompanying drawings. FIG. 3 is a cross-sectional view showing a mixing/charging port for medical treatment of an embodiment according to the present invention. In FIG. 3, reference numeral 4 denotes an insertion member, 5 denotes an annular rib, 7 denotes a seating, 8 denotes a passage and 9 denotes a hook. The mixing/charging port for medical treatment of FIG. 3 is the same as in FIG. 1 in that the valve 1 is sandwiched between the hook 9 of the cover 2 and the annular rib 5.

Figure 1C:
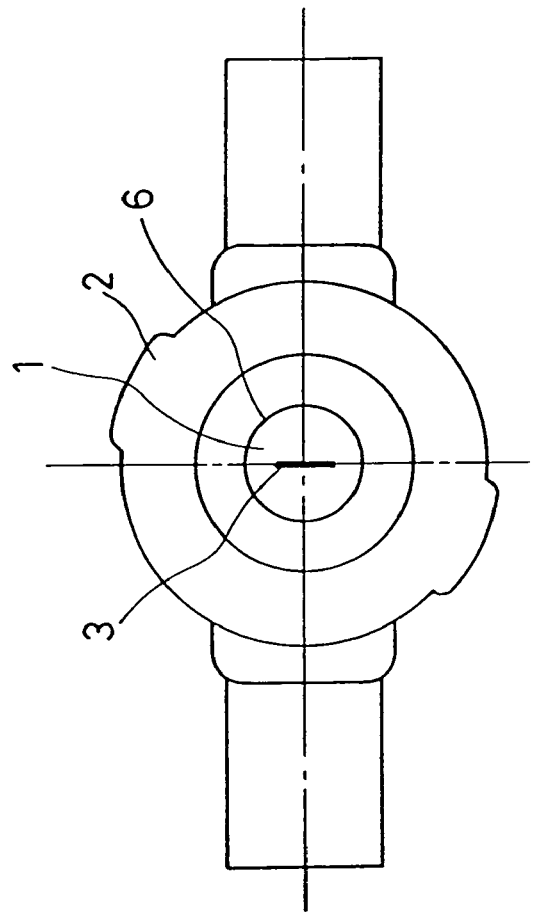
FIG. 1C is a conventional plan view of the mixing/charging port.
Figure 1A:
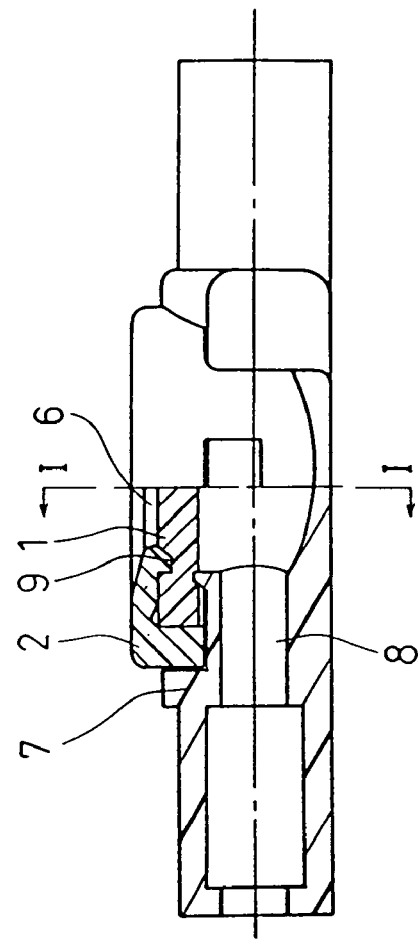
FIG. 1A is a longitudinal sectional view of a conventional mixing/charging port.
Figure 1B:
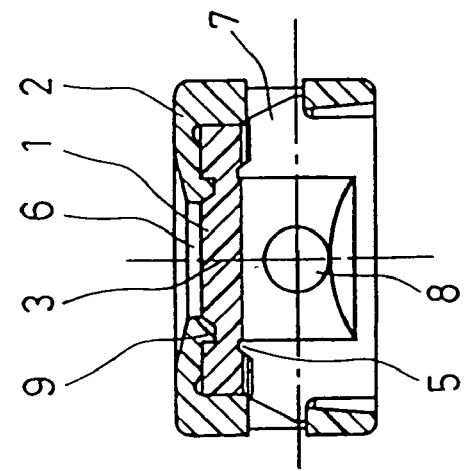
FIG. 1B is a cross sectional view of the mixing/charging port along line I-I in FIG. 1A.

The mixing/charging port for medical treatment of FIG. 3 is different from that of FIG. 1 in that the inner side surface of the seating 7 is formed to have the same shape as a state in which the depressed part of the valve 1 is depressed with the insertion member 4 inserted therein. In other words, in the conventional mixing/charging port, since there is a certain space between the inner bottom surface of the seating 7 and the tip of the depressed part of the valve 1, an air bubble, which has been generated spontaneously or is a contaminant due to the working error, gets into the space, thus making it difficult to absorb air bubbles from the insertion member 4.

In FIG. 3, the inner side surface of the seating 7 has a concave shape that matches to the shape in a state in which the valve 1 is depressed by the insertion member 4. Therefore, the depressed part of the valve 1 enters the concave part entirely, and thus a space for air bubbles to be able to enter is not present. Therefore, it is possible to prevent the retention of air bubbles from occurring.

Furthermore, in order to facilitate the matching of the inner side face of the seating 7 to the shape of the depressed part of the valve 1, it is preferable that the deformation allowance of the material forming the valve 1 is sufficiently large. Thus, it is possible completely to avoid generating the regions in which air bubbles can be retained, and to carry out medical treatment more safely.

Figure 2:
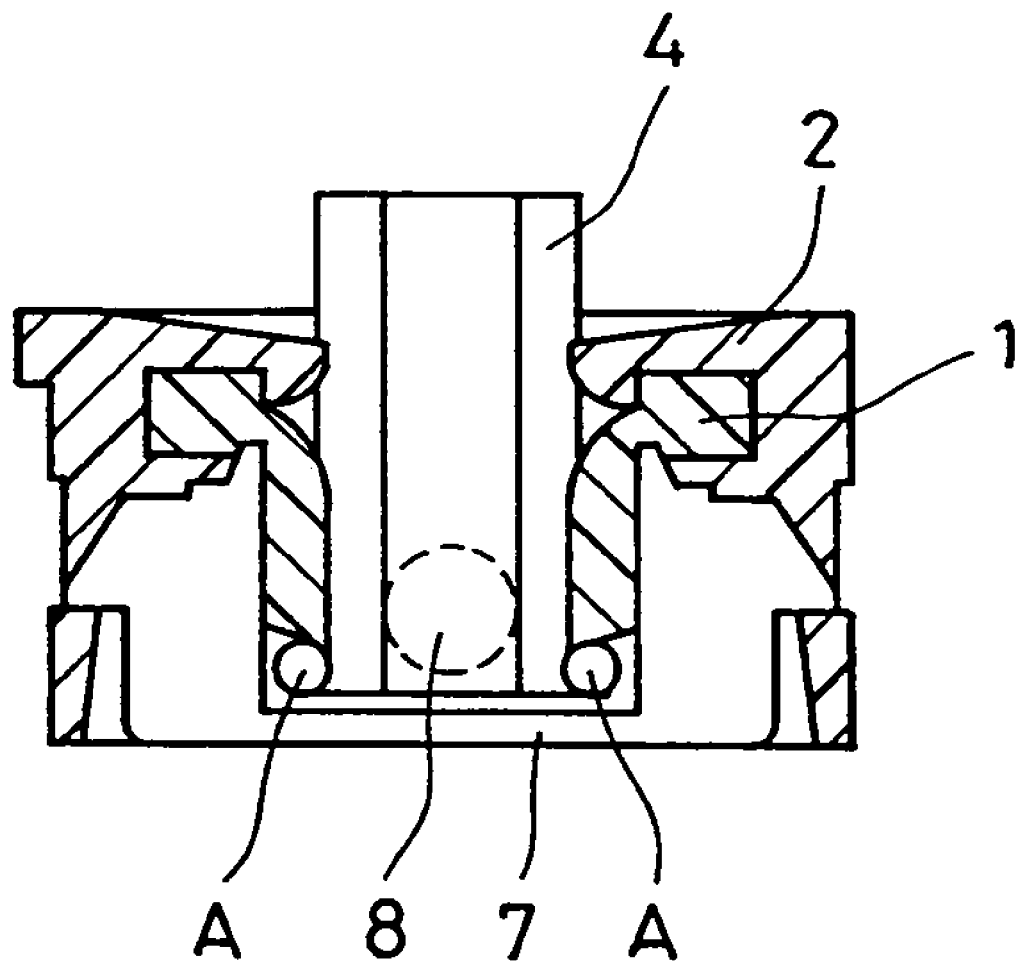
FIG. 2 is a cross-sectional view showing a conventional mixing/charging port for medical treatment.

Furthermore, in order not to generate the region A in FIG. 2, it is sufficient that the inner bottom surface of the seating 7 is brought into contact against the depressed part of the valve 1. Thus, it is possible to avoid generating the region A in which air bubbles are retained, thus making it possible to prevent air bubbles from generating.

However, in the case where there are air bubbles that have entered and remained, the above-mentioned configuration may obstruct the insertion of the insertion member. The inner bottom surface of the seating 7 may be provided with a groove for removing air bubbles and securing the passage. It is preferable that the groove is provided in the flowing direction of the mixing/charging port and the bottom part of the passage 8 (including the groove) is located at a lower level relative to the bottom surface of the seating 7. From the viewpoint of the manufacturing cost, it is preferable that the shape of the cross section of the passage 8 corresponds to a shape defined by a chord and a bottom part of the cross section of the arc at the bottom part of the cross section of the opening of the passage 8.

With such a configuration, the air bubbles present can be ejected to the outside through the passage 8 by the priming etc., or air bubbles are retained in the groove in a lower part of the insertion member. Thus, it is possible to absorb air bubbles to the outside of the mixing/charging port through the insertion member 4.

Therefore, with such a configuration, air bubbles generated in the mixing/charging port or present as a contaminant in the mixing/charging port can be absorbed by inserting the insertion member deeply into the mixing/charging port. Therefore, it is possible to avoid the risk that air bubbles are infused into the patient when transfusing blood or infusing a drug solution is carried out.

Figure 4A:
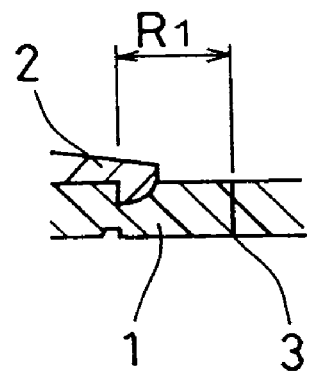
FIG. 4 is a cross-sectional view showing a mixing/charging port for medical treatment of an embodiment according to the present invention.
Figure 4B:
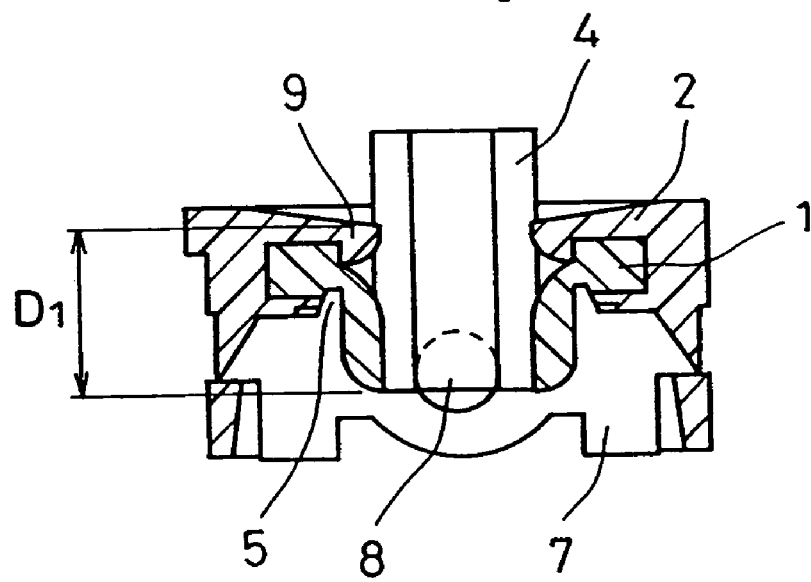

Moreover, if the bottom surface of the seating 7 is located in an extremely high level, the depressed part of the valve reaches the bottom surface, which may obstruct the insertion of the insertion member. For example, as shown in FIG. 4A, the distance between the annular rib 5 and the slit 3 is represented by $R_1$, and as shown in FIG. 4B, the distance between the upper end of the fitting hole 6 formed with the cover 2 and the bottom surface of the seating 7 is represented by $D_1$. In the case that $R_1$ is set to be about 3 mm and $D_1$ is set to be 5.3 to 5.5 mm, it is confirmed experimentally that as long as $D_1$ and $R_1$ satisfy the following relationship (Formula 1), the insertion member 4 can be inserted without difficulty.

$$1.75R_1 \leq D_1 \leq 1.85R_1 \qquad \text{(Formula 1)}$$

The invention may be embodied in other forms without departing from the spirit or essential characteristics thereof. The embodiments disclosed in this application are to be considered in all respects as illustrative and not limitative, the scope of the invention is indicated by the appended claims rather than by the foregoing description, and all changes which come within the meaning and range of equivalency of the claims are intended to be embraced therein.

What is claimed is:

1. A mixing/charging port for medical treatment comprising:
   a disk-like valve having a slit that forms an insertion hole at the center,
   a seating for supporting a rear surface of the periphery of the valve with the center of the rear surface of the valve left unsupported, the seating having a concave covered by the valve and a passage laterally passing through the concave, and
   a cover for restraining the valve by covering a front surface of the periphery of the valve with the center of the front surface of the valve left uncovered, wherein:
   an inner periphery forming a fitting hole of the cover works as an anchor for anchoring an insertion member to the mixing/charging port in a way in which the insertion member is fitted to the fitting hole when the insertion member is inserted into the slit,
   wherein when the insertion member is inserted into the slit so as to split edges formed by the slit of the valve, a part along the edges is depressed by the insertion member, and a tip of the depressed part of the valve is brought into contact against an inner bottom surface of the concave of the seating.

2. The mixing/charging port for medical treatment according to claim 1, wherein the inner side surface of the seating is formed so as to have the same shape as the shape of the valve in a state in which the valve is depressed by the insertion of the insertion member.

3. The mixing/charging port for medical treatment according to claim 2, wherein a groove is provided in the direction of the flow through the inner part of the mixing/charging port so that the bottom surface of the passage is located in level to the bottom surface of the seating.

4. The mixing/charging port for medical treatment according to claim 3, wherein the cross-sectional shape of the groove corresponds to the shape surrounded by the arc and chord at one of the opening part of the passage.

5. The mixing/charging port for medical treatment according to claim 1, wherein a groove is provided in the direction of the flow through the inner part of the mixing/charging port so that the bottom surface of the passage is located in a lower level to the bottom surface of the seating.

6. The mixing/charging port for medical treatment according to claim 5, wherein the cross-sectional shape of the groove corresponds to the shape surrounded by the arc and chord at one of the opening part of the passage.

* * * * *